US005989202A

United States Patent [19]

Noda et al.

[11] Patent Number: 5,989,202

[45] Date of Patent: Nov. 23, 1999

[54] MEDICAL ULTRASONIC GENERATOR

[75] Inventors: Kenichi Noda, Nagoya; Toshihiko Yayama, Saga-ken; Etsuo Matsumoto, Nagoya, all of Japan

[73] Assignee: TEN Kabushiki Kaisha, Nagoya, Japan

[21] Appl. No.: 09/037,459

[22] Filed: Mar. 10, 1998

[30] Foreign Application Priority Data

Mar. 18, 1997 [JP] Japan .................................... 9-085927

[51] Int. Cl.[6] ........................................................ A61N 7/00

[52] U.S. Cl. ................................. 601/2; 310/322; 310/26

[58] Field of Search ............................ 601/1, 2; 600/439, 600/372; 310/26, 370, 322; 607/1, 2, 145, 152, 154; 604/20

[56] References Cited

U.S. PATENT DOCUMENTS

| | | | |
|---|---|---|---|
| 2,728,869 | 12/1955 | Pohlman | 310/26 |
| 3,170,102 | 2/1965 | Hayes | 318/118 |
| 3,357,684 | 12/1967 | Kunnen | 310/26 |
| 3,828,769 | 8/1974 | Mettler | 601/2 |
| 4,269,176 | 5/1981 | Beyer et al. | 128/24 A |
| 4,530,360 | 7/1985 | Duarte | 601/1 |
| 5,070,316 | 12/1991 | Engdahl et al. | 335/215 |
| 5,558,623 | 9/1996 | Cody | 601/2 |
| 5,823,962 | 10/1998 | Schaetzle et al. | 601/2 |

FOREIGN PATENT DOCUMENTS

| | | | |
|---|---|---|---|
| 10-70392 | 10/1998 | Japan | H05K 9/00 |

*Primary Examiner*—Nestor Ramirez
*Assistant Examiner*—B Mullins
*Attorney, Agent, or Firm*—Frishauf, Holtz, Goodman, Langer & Chick, P.C.

[57] ABSTRACT

A medical ultrasonic generator having an ultrasonic radiator wound with coils connected to a high-frequency oscillator, when the radiator is provided with a sintered element consisting essentially of Ni—Zn having a thickness of 8 to 20 mm. The ferrite element can effectively apply the ultrasonic oscillation to a human body to improve the effect of medical treatment. Further, the medical ultrasonic generator is superior in terms of workability as a medical treatment because of its ability to effectively apply the ultrasonic oscillation to the affected part even through the clothing worn by a patient.

4 Claims, 3 Drawing Sheets

MEDICAL ULTRASONIC GENERATOR

BACKGROUND OF THE INVENTION

1. Field of the Invention

The present invention relates to a medical ultrasonic generator which is able to efficiently improve an affected body part.

2. Description of the Prior Art

In recent years, several kinds of medical ultrasonic generators have been used at medical sites to apply ultrasonic oscillation to an affected human body part so as to relax muscles or to quicken the circulation of blood. Those kinds of medical ultrasonic generators must be used in direct contact with the affected body part on which ultrasonic gel is coated, so that they could not apply the ultrasonic wave to the affected body part of a patient wearing clothes. As a result, they are inferior in terms of workability as a medical treatment because they required undressing of the patient and the application of the ultrasonic gel.

The present applicant has found that a ferrite material composed of ferric oxide ($Fe_2O_3$) as a principal component containing nickel-zinc or manganese-zinc, etc. has the characteristics to absorb electromagnetic waves generated from several kinds of electronic and electric appliances such as cell phones, computers, etc. and to transform them into beneficial waves for organisms including human bodies. Accordingly, the present applicant has filed Patent Application No. 8-247303 on Aug. 28, 1996. This application, which was published on Mar. 10, 1998 as Japanese Publication No. 10-70392, discloses a transformer for injurious waves is made of dielectric synthetic resin containing a wave-transforming material of about 30–95 wt %. The wave-transforming material contains ferrite powder as a principal component. The transformer may be made into a required form to be attachable to a human body or an electronic appliance.

SUMMARY OF THE INVENTION

The present invention has been developed by observing the above-described characteristics of the ferrite material to absorb electromagnetic waves, and an object of the present invention is to provide a medical ultrasonic generator which can improve the effect of medical treatment absorbing electromagnetic waves radiating from a human body.

It is another object of the present invention to provide a medical ultrasonic generator which can improve an affected body part by effective application of ultrasonic oscillation to an affected body part even through worn clothing by a patient.

To accomplish those objects, the medical ultrasonic generator of the present invention comprises an ultrasonic radiator wound with coils connected to a high-frequency oscillator wherein the radiator is provided with a sintered ferrite element consisting essentially of Ni-Zn having a thickness of 8 to 20 mm.

When the coils are energized with high-frequency pulse current to generate ultrasonic oscillation from the radiator, the ultrasonic oscillation is amplified by the ferrite element to be transformed into ultrasonic waves that are readily absorbed in the affected body part.

DETAILED DESCRIPTION OF THE PREFERRED EMBODIMENTS

Figure 1:
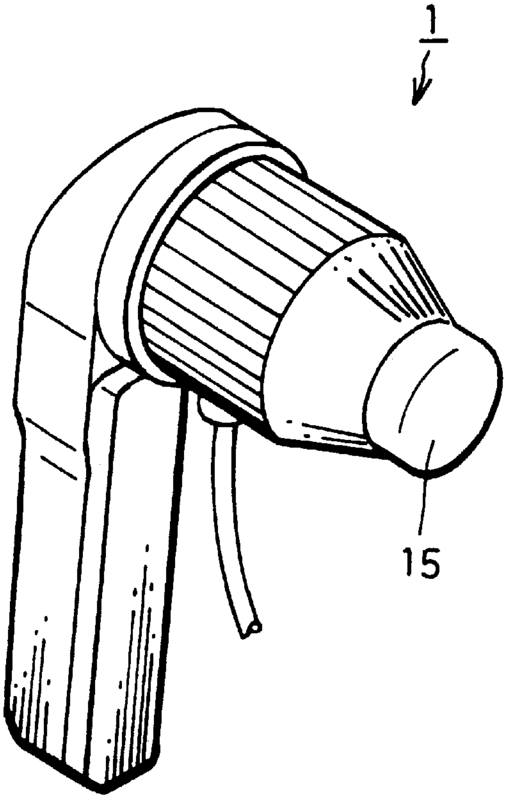
FIG. 1 is a perspective view of a medical ultrasonic generator according to the invention.

Referring to FIG. 1 to FIG. 5, a first embodiment of the present invention will be described hereinafter.

In the drawings, there is shown a medical ultrasonic generator 1, in which an ultrasonic radiator 5 is incorporated that is wound with high-frequency coils 3. When the ultrasonic coils 3 are energized with high-frequency pulse current from a high-frequency oscillator (not shown), the ultrasonic radiator 5 generates ultrasonic oscillation of a required output power (intensity) in a required frequency of 1 MHz to 10 MHz, for example.

The ultrasonic frequency and output power of the ultrasonic radiator 5 are defined in accordance with objects of a medical treatment and applying conditions of the medical ultrasonic generator 1 such as home use or application in medical facilities; the ultrasonic frequency is properly selected in the range described above.

Incidentally, the ultrasonic radiator 5 may be a known magnetostrictive oscillator composed of a magnetic substance wound with high frequency coils or a known electrostrictive oscillator utilizing electrostatic strain of multicrystalloid material.

Also, the medical ultrasonic generator 1 may be one that is capable of switching or varying the frequency and the output power to be generated.

To the front surface of the ultrasonic radiator 5 is stuck a ferrite element 9 through an elastic thin plate 11 of silicone rubber.

Figure 2:
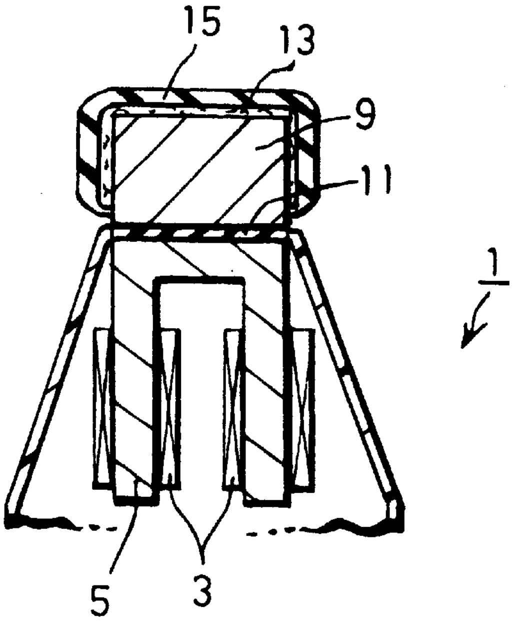
FIG. 2 is a vertical sectional view of the medical ultrasonic generator.

The elastic thin plate 11 serves as a cushion when the medical ultrasonic generator 1 is pressed to a human body for the medical treatment. If the plate 11 is made too thick, there is a fear that the ultrasonic oscillation from the ultrasonic vibrator 5 may be damped. Accordingly, it is desirable that the elastic thin plate 11 is made thin within the range where the cushion effect can be attained. The ferrite element 9 is a sintered ferrite plate, as shown in FIG. 2, composed of ferric oxide ($Fe_2O_3$) as a principal component containing nickel-zinc, manganese-zinc, etc. and sintered in 3–20 mm thickness at about 1000° C. The thickness of the ferrite element 9 is determined in accordance with the frequency of ultrasonic wave radiated from the ultrasonic radiator 5. In case of the ultrasonic frequency in 1 MHz, for example, the thickness is set in 3 mm and in contrast with this, in case of the frequency in 10 MHz, it is set in 20 mm. Further, since the ultrasonic frequency is determined in accordance with kinds of the affected body part and conditions of the medical treatment as described above, the optimum thickness of the ferrite element 9 is determined in accordance with those factors.

Figure 3:
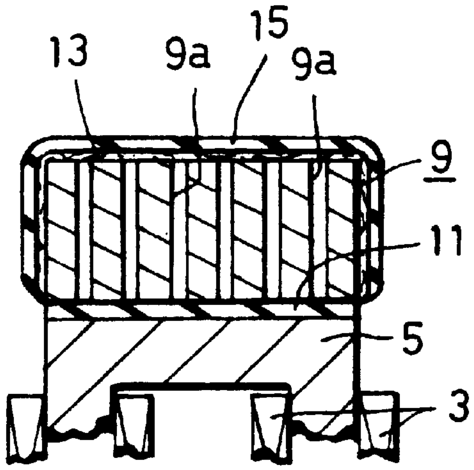
FIG. 3 is a diagram of another ferrite element.
Figure 4:
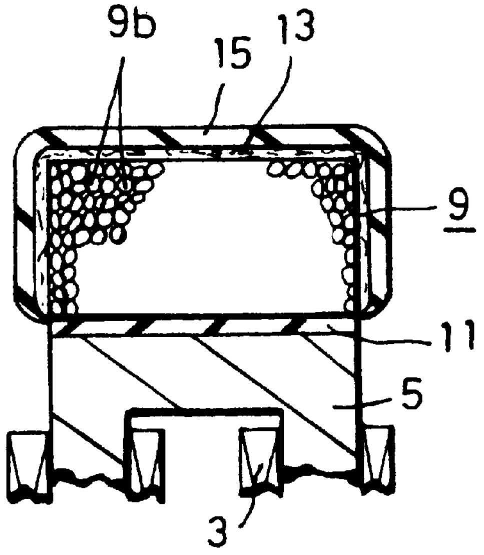
FIG. 4 is a diagram of still another ferrite element.
Figure 5:
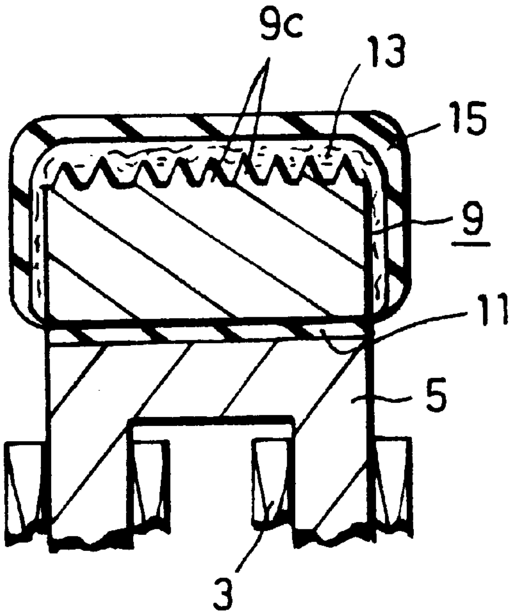
FIG. 5 is a diagram of a further ferrite element.

Further, the ferrite element 9 may be a sintered ferrite plate in the shape of a grid in which a number of gap portions 9*a* are longitudinally and laterally arranged at required intervals, as shown in FIG. 3; a sintered ferrite plate which is made of ferrite particles 9*b* of 1–3 mm in the mean diameter of a particle solidified into a plate of 3–20 mm thickness, as shown in FIG. 4; or a sintered ferrite plate which is made in a required thickness and provided with a number of projections 9$c$, pyramid or cone in shape (FIG. 5 shows a cone type), on the front surface, as shown in FIG. 5.

Further, on the front surface (including the peripheral surface) of the ferrite element 9 is coated a metal sheet 13 made of copper-fiber nonwoven fabric, etc. of a required thickness (1 to 3 mm). The top surface of the metal sheet 13 is entirely coated with an elastic coating member 15 of silicone rubber or the like.

The metal sheet 13 and the elastic coating member 15 serve as cushions for a human body when the medical ultrasonic generator 1 is in use but are not always required. However, the medical ultrasonic generator 1 with an exposed metal sheet 13 also has a function to discharge static electricity charged on clothing worn by the patient. Incidentally, the metal sheet 13 may be nonwoven fabric of metal-coating fiber which is composed of synthetic-resin fiber coated with metal film such as copper or the like.

In the medical ultrasonic generator 1, when the high-frequency coils 3 are energized with high-frequency pulse current to generate ultrasonic oscillation from the radiator 5, the ultrasonic oscillation is amplified by the ferrite element 5 to generate a new ultrasonic oscillation, and the new ultrasonic oscillation acts on a human body through the metal sheet 13 and the elastic coating member 15. The amplified ultrasonic oscillation acts on the affected body part even through clothes.

Next, some examples will be described of the medical treatment by use of the medical ultrasonic generator 1.

The ferrite element 9 of the medical ultrasonic generator 1 to be used in the test examples 1 to 5 is composed of a sintered ferrite plate which is 20 mm in thickness and formed in a grid shape. The output frequency from the ultrasonic radiator 5 was regulated in 1 MHz and the output power in 0.5 w/cm2. In the respective examples 1 to 5, the temperature was observed by a thermography of each point on the human body before the use of the above-described medical ultrasonic generator 1, as was done of each point on the human body after the application of the generator 1 for about 5–15 minutes to the sacrum through clothing worn by the patient. The results are as follows:

| | |
|---|---|
| Test Example 1 | |
| Temperature of each point on the human body before use; | |
| a: 29.5° C. | b: 31.1° C. |
| c: 27.5° C. | d: 29.3° C. |
| Temperature of each point on the human body after use; | |
| a: 33.0° C. | b: 33.6° C. |
| c: 32.8° C. | d: 33.5° C. |
| Test Example 2 | |
| Temperature of each point on the human body before use; | |
| a: 29.3° C. | b: 30.3° C. |
| c: 30.7° C. | d: 30.2° C. |
| Temperature of each point on the human body after use; | |
| a: 33.7° C. | b: 33.3° C. |
| c: 33.5° C. | d: 33.2° C. |
| Test Example 3 | |
| Temperature of each point on the human body before use; | |
| a: 22.4° C. | b: 32.0° C. |
| c: 33.0° C. | d: 32.9° C. |
| Temperature of each point on the human body after use; | |
| a: 32.9° C. | b: 33.5° C. |
| c: 33.6° C. | d: 33.6° C. |

-continued

| | |
|---|---|
| Test Example 4 | |
| Temperature of each point on the human body before use; | |
| a: 29.8° C. | b: 27.6° C. |
| c: 28.7° C. | d: 27.1° C. |
| Temperature of each point on the human body after use; | |
| a: 33.2° C. | b: 33.0° C. |
| c: 33.2° C. | d: 33.0° C. |
| Test Example 5 | |
| Temperature of each point on the human body before use; | |
| a: 28.7° C. | b: 30.2° C. |
| c: 27.4° C. | d: 28.6° C. |
| Temperature of each point on the human body after use; | |
| a: 33.0° C. | b: 33.2° C. |
| c: 33.0° C. | d: 33.3° C. |

In any of the test examples 1–5, even when the medical ultrasonic generator 1 was applied through clothing worn by the patient, the temperature of each point was raised as well as when the ultrasonic treatment was applied directly to the affected body part. Namely, the ultrasonic oscillation generated from the medical ultrasonic generator 1 acted on the affected part of a human body even through clothes and quickened the circulation of blood to improve the affected body part.

Next, the second embodiment will be described referring to FIG. 6. Incidentally, the same elements as those of the first embodiment are given the same reference numerals, and explanation of these elements is omitted.

Figure 6:
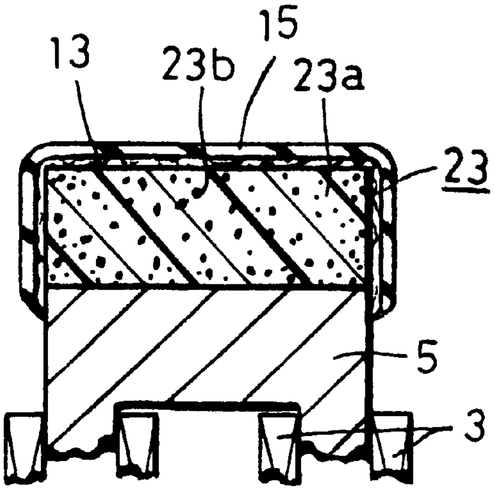
FIG. 6 is a diagram of a still further ferrite element.

In FIG. 6, there is shown a medical ultrasonic generator 21, in which an ultrasonic radiator 5 is provided with an elastic ferrite element 23. On the top surface of the elastic ferrite element 23 is secured a metal sheet 13 and an elastic coating member 15, if necessary. The elastic ferrite element 23 is composed of silicone rubber 23$a$ which contains sintered ferrite particles 23$b$ of 1–5 μm in the mean diameter in about 85–95 wt % and is solidified into a plate of 3–15 mm thickness. The content of the wintered ferrite particles 23$b$ is determined in accordance with an oscillating frequency of the ultrasonic radiator 5; for instance, in case of the oscillating frequency in 1 MHz, the content is set in a small amount, and in contrast with this, in case of the frequency in 10 MHz, it is set in a large amount. However, when the content is set over 95 wt %, the elastic ferrite element 23 can not be held in a plate form. Further, the thickness of the elastic ferrite element 23 is also determined in accordance with the oscillating frequency; in case of the oscillating frequency in 1 MHz, the thickness is set in about 3 mm, and in contrast with this, in case of the frequency in 10 MHz, it is set in about 20 mm.

In the medical ultrasonic generator 21 described above, when the oscillating frequency of the ultrasonic oscillator 5 is set in 3 MHz, the output power in 0.5 w/cm2, the thickness of the elastic ferrite element 23 in 8 mm, and the content in 90 wt %, an effect could be accomplished similarly to the effects in the examples 1–5 described above.

What is claimed is:

1. A medical ultrasonic generator having an ultrasonic radiator wound with coils connected to a high-frequency oscillator, wherein said radiator is provided with a sintered ferrite element consisting essentially of Ni-Zn having a thickness of 8 to 20 mm.

2. A medical ultrasonic generator as defined in claim 1 wherein said sintered ferrite element comprises a sintered ferrite plate including gap portions arranged in a grid.

3. A medical ultrasonic generator as defined in claim 1, wherein said sintered ferrite element comprises a plate solidified from a number of sintered Ni-Zn ferrite particles.

4. A medical ultrasonic generator as defined in claim 1, wherein said sintered ferrite element is coated with a metal-fiber fabric.

* * * * *